United States Patent [19]

Schanzer

[11] Patent Number: 4,619,641
[45] Date of Patent: Oct. 28, 1986

[54] COAXIAL DOUBLE LUMEN ANTERIOVENOUS GRAFTS

[75] Inventor: Harry Schanzer, Larchmont, N.Y.

[73] Assignee: Mount Sinai School of Medicine of The City University of New York, New York, N.Y.

[21] Appl. No.: 670,827

[22] Filed: Nov. 13, 1984

[51] Int. Cl.$^4$ .............................................. A61M 5/00
[52] U.S. Cl. ........................................ 604/8; 604/86; 604/244; 138/103
[58] Field of Search .......................... 3/1.4; 604/8–10, 604/86, 175, 201, 414, 415, 905; 128/764, DIG. 21; 138/103

[56] References Cited

U.S. PATENT DOCUMENTS

| | | | |
|---|---|---|---|
| 2,653,606 | 9/1953 | Ryan | 604/414 |
| 3,566,868 | 3/1971 | Baptist et al. | 138/103 |
| 3,814,137 | 6/1974 | Martinez | 604/86 |
| 4,076,023 | 2/1978 | Martinez | 604/86 |
| 4,184,489 | 1/1980 | Burd | 604/86 |

OTHER PUBLICATIONS

Manual of Vascular Access, Organ Donation, and Transplantation, *Arteriovenous Communication: Bridge Grafts*, Samuel K. S. So, Chapter 7, p. 60.
Manual of Vascular Access, Organ Donation, and Transplantation, *Aneurysm and Pseudoaneurysm*, p. 82.
JAMA, vol. 249, No. 2, Jan. 14, 1983, *Polytetrafluoroethylene Graft Survival in Hemodialysis*, Munda et al., pp. 219–222.
Cardiovascular Diseases, Bulletin of the Texas Heart Institute, vol. 7, No. 1, Mar. 1980, *Modified Human Umbilical Vein Graft Anteriovenous Fistulae as a Source of Angioaccess in Maintenance Hemodialysis*, Rubio et al., pp. 51–57.
The Journal of Cardiovascular Surgery, vol. 21, No. 2, Mar.-Apr. 1980, *Experience with Arterial Substitutes in the Construction of Vascular Access for Hemodialysis*, Haimov et al. pp. 149–154.
Dialysis & Transplantation, vol. 9, No. 4, Apr. 1980, *A Critical Appraisal of the Changing Approaches to Vascular Access for Chronic Hemodialysis*, Hammill et al., pp. 325–328.
Surgery, vol. 88, No. 5, *Medium-Term Follow-Up of Forty Autogenous Vein and Forty Polytetrafluoroethylene (Gore-Tex) Grafts for Fascular Access*, Jenkins et al., pp. 667–672.
Arch. Surg., vol. 119, Nov. 1984, *Complications of Renal Dialysis Access Procedures*, Connolly et al., pp. 1325–1328.
Advances In Therapy, vol. 1, No. 2, Mar. 1984, *Early Clinical Experience with a New PTFE Graft in The A-V Fistula Position*, Franklin, pp. 110–114.
Br. J. Surg., vol. 67, (1980), *The Complications of Arteriovenous Grafts for Vascular Access*, Guillou et al. pp. 517–521.

Primary Examiner—C. Fred Rosenbaum
Assistant Examiner—Jerome R. Smith, Jr.
Attorney, Agent, or Firm—Brumbaugh, Graves, Donohue & Raymond

[57] ABSTRACT

A coaxial double lumen tube for use in hemoaccess which comprises an outer tube positioned over an inner tube, both tubes having an internal and external diameter and a wall thickness, the outer tube having an internal diameter which is at least 1 mm larger than the external diameter of the inner tube creating a space between the outer tube and the inner tube and a self-sealing, nonbiodegradeable, biocompatible polymer adhesive which evenly fills the space between the outer tube and the inner tube.

6 Claims, 3 Drawing Figures

COAXIAL DOUBLE LUMEN ANTERIOVENOUS GRAFTS

BACKGROUND OF THE INVENTION

Dialysis treatment for patients with renal failure require a ready access to blood vessels in order for blood to be continuously withdrawn from the patient in amounts of over 200 ml/min. The blood withdrawn from the patient is passed through a dialysis machine, and returned to the patient. A very common method of producing this hemoaccess is the use of expanded polytetrafluorethylene (PTFE) tubes as grafts which are surgically placed between an artery and a vein (PTFE AV fistula). This procedure is especially useful in patients who do not have blood vessels which will support the construction of a more traditional primary fistula on the forearm.

These PTFE grafts cannot be used safely to withdraw blood however until they have been in place for a minimum of 14 days after surgery and have become surrounded by fibrotic tissue. Because of the bleeding which occurs at the site of a needle puncture in these grafts if fibrotic tissue is absent, common complications encountered with early puncturing of PTFE AV fistulas are a hematoma surrounding the graft, false aneurysm and possible graft occlusion. The Atlas of Angioaccess Surgery by Pedro A. Rubio and Edward M. Farrell (Year Book Medical Publishers, Inc., 1983), which is incorporated herein by reference, states that "graft fistulas should not be punctured before the third postoperative week. Earlier puncture risks hematoma formation in the subcutaneous tunnel following needle withdrawal, which will result in further delay in healing." Various materials in addition to PTFE have been tried including autologous saphenous vein, Dacron, synthetic polyester fiber velour, modified bovine carotid xenograft, and modified human umbilical vein, but none have overcome the problems associated with early puncture of the graft.

A coaxial double lumen tube for use in hemoaccess wherein the space between the two lumen is filled with a self-sealing, nonbiodegradeable polymer (hereinafter "filled double tubes") has now been discovered. The filled double tube does not bleed upon puncture with a dialysis needle even immediately after surgery. Ex vivo perfusion tests and AV fistula experiments in dogs clearly show that the filled double tubes are superior as grafts to the known single PTFE tube in the amount of bleeding resulting from puncture of the tube with a dialysis needle.

The advantages of the filled double tube are that (1) it can be used for hemoaccess immediately after implantation, (2) the lack of bleeding results in a lower incidence of perigraft hematomas and a lower incidence of pseudoaneurysms, (3) the lack of bleeding upon puncture obviates the need for prolonged compression of the puncture site with secondary occlusion of the tube, and (4) due to the increased rigidity of the filled double tube, puncturing of the tube is easier.

SUMMARY OF THE INVENTION

A coaxial double lumen tube for use in hemoaccess which comprises an outer tube positioned over an inner tube, both tubes having an internal and external diameter and a wall thickness, and the outer tube having an internal diameter which is at least 1 mm larger than the external diameter of the inner tube creating a space between the outer tube and a self-sealing, nonbiodegradeable, biocompatible polymer which evenly fills the space between the outer and inner tubes has now been discovered.

DESCRIPTION OF PREFERRED EMBODIMENT

Figure 1:
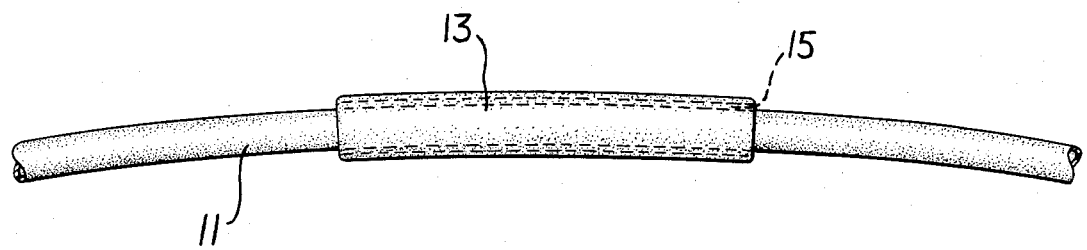
FIG. 1 is a plan view of the claimed filled double tube.
Figure 2:
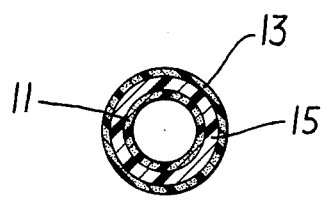
FIG. 2 is a cross-sectional view of the claimed filled double tube.

As illustrated in FIGS. 1 and 2, the filled double tube comprises an inner tube 11 and an outer tube 13 which is positioned over the center portion of the inner tube leaving a space 15 between the inner and outer tube 13 and allowing the ends of the inner tube to extend equally beyond the ends of the outer tube. The space 15 is filled with a self-sealing, nonbiodegradeable, biocompatible polymer (hereinafter "polymer") for example a silicone rubber sealant (Dow Corning Catalogue No. 732-3).

The inner tube 11 can have an internal diameter from about 4 mm to 8 mm with 6 mm being the preferred internal diameter and a wall thickness of about 0.5 to 1 mm. The outer tube 13 can have an internal diameter from about 6 mm to 10 mm which is at least 1 mm larger than the external diameter (internal diameter + wall thickness) of the inner tube with 8 mm being the preferred internal diameter and a wall thickness of about 0.5 mm to 1 mm, preferably 1 mm. The wall thickness of the inner and outer tubes may be the same or different.

The length of the inner tube 11 depends on the specific application for the tube, and the site in the patient at which the filled double tube is implanted. As a result, the inner tube 11 can vary in length from 100 mm to 500 mm with 150 mm being the preferred length for looped forearm grafts. The length of the outer tube 13 is equal to or less than that of the inner tube 11 and can vary in length from 60 mm to 400 mm with 100 mm being the preferred length for forearm grafts. The inner tube 11 can be made from any hemocompatible material suitable as a conduit. Suitable material for the inner and outer tubes are for example, Teflon PTFE, and Dacron synthetic polyester fiber. The outer tube 13 can be made from any biocompatible material suitable as a conduit. Examples of suitable materials are, Teflon PFTE and Dacron synthetic polyester fiber. Preferably, the filled double tube is made entirely from GORE-TEX reinforced PTFE tubing developed by W. F. Gore & Associates, Inc. by rapidly stretching highly crystalline unsintered polytetrafluorethylene.

The filled double tube can be used for any medical technique in which repeated hemoaccess is required, for example, but without intending to limit the possible applications, intravenous drug administration, chronic insulin injections, chemotherapy, frequent blood samples, connection to artificial lungs and hyperalimentation.

The filled double tube is ideally suited for use in chronic hemodialysis access for example in a looped forearm graft fistula, straight forearm graft fistula, straight arm graft fistula, looped thigh graft fistula and axillaryaxillary graft fistula or any other AV fistula application. Because of its hard consistency and resistance to collapse, the filled double tube may also be useful for among other things, arterial bypasses subjected to external pressure (for example, axillo-femoral, axillo-axillo bypasses) and other replacement surgery.

In an alternate embodiment of the invention, the inner surface of the outer tube and the outer surface of the inner tube may be rough to prevent possible separation of the polymer from the tube surface during use.

The filled double tubes used in the following Examples (2–3) were prepared by the procedures outlined in Example 1. The same procedure can be used to prepare filled double tubes of various sizes and lengths.

EXAMPLE 1

A 150 mm segment of a 6 mm internal diameter thick GORE-TEX reinforced PTFE tube was placed over a metallic rod. The rod had a diameter of 6 mm and fit the lumen of the tube tightly. A 70 mm segment of a 8 mm internal diameter thick GORE-TEX reinforced PTFE tube was placed over the inner tube with the rod in its lumen. The outer tube was centered over the inner tube in order to leave about 40 mm of the inner tube free on both ends.

One of the ends of the outer tube was sealed with silicone rubber sealant (Dow Corning Cat. #732-3) by using a 5 ml syringe filled with silicone sealant and equipped with an angiocatheter. After allowing the tubes to stand for 24 hours the sealant was cured and the opening at one end was completely sealed. The remaining space between the inner and outer tubes was filled by diluting silicone sealant 3:1 (w/v) with acetic acid and placing the diluted silicone sealant in a 5 cc syringe equipped with a 2 mm diameter catheter. The catheter was inserted into the remaining space between the tubes from the unsealed end and the syringe was placed in a Harvard pump.

The pump injected the silicone into the unsealed end and the catheter was slowly withdrawn. As soon as excess sealant began to appear at the open end, injection was discontinued. The filled double tube was then rolled on a smooth surface to distribute the silicone uniformly in the space between the tubes and after setting for an additional 24 hours the silicone sealant was cured and the silicone filled double tube was removed from the metallic rod and was ready for use.

EXAMPLE 2

A 60 mm double tube having as an inner tube a 4 mm internal diameter GORE-TEX PTFE thin tube and as an outer tube a coaxial 6 mm thick GORE-TEX PTFE tube with the space between the tubes filled with silicone rubber sealant ("filled double") was employed. For comparison the following control tubes of the same lengths were used: (1) an unfilled double tube using a 4 mm inner thin wall GORE-TEX PTFE tube and a 6 mm outer thick wall GORE-TEX PTFE tube without silicone in the space between the tubes ("double"), (2) a thin 4 mm conventional GORE-TEX PTFE tube ("thin"), and (3) a thick 6 mm conventional GORE-TEX PTFE tube ("thick"). Four dogs were used in this experiment.

A Scribner shunt was placed between the femoral artery and the femoral vein in each dog. Each of the tubes to be tested was placed between the arterial and venous branches of the shunts. The four different types of tubes were inserted three times in various sequences in each dog (12 measurements per dog).

Figure 3:
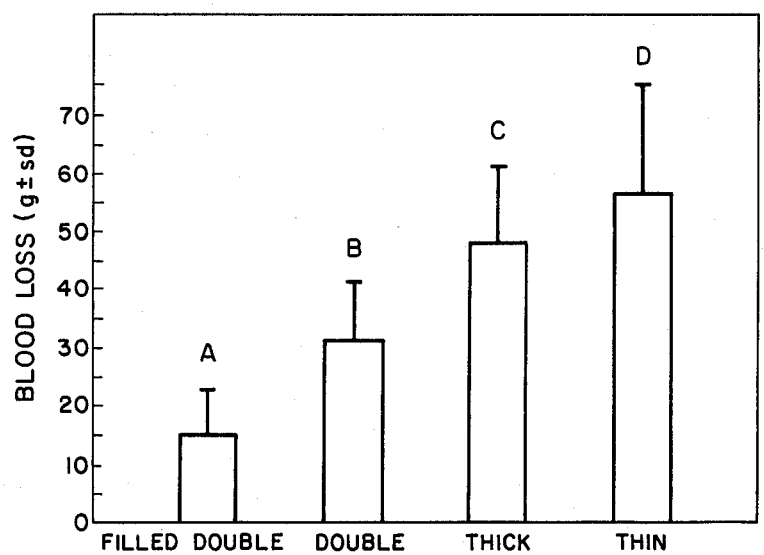
FIG. 3 is a chart which compares the blood loss from the filled double tube when used as a graft for hemoaccess with the blood loss from other conventional grafts.

Puncturing was performed in each case by piercing the tube with an 18-gauge needle. Intraluminal pressure measurements were carried out with each puncture in order to be certain that the tube was open and that the pressure condition remained constant. After removing the needle, each tube puncture site was allowed to bleed freely into a cup for 30 seconds. The Scribner shunt was then clamped and the tube changed. The amount of bleeding was measured by weighing the cup before and after bleeding. The results of these experiments are set forth in Tables 1, 2 and 3 and FIG. 3 and clearly demonstrate a very significant reduction in bleeding after puncture ex vivo using the new filled double tube ("filled double") for the graft.

TABLE 1

HEMODIALYSIS ACCESS (GORE-TEX ® PTFE GRAFTS)
Ex-Vivo Bleeding Tests

| | Graft Type | Blood Pressures | Blood Weights | m ± sd |
|---|---|---|---|---|
| Leg #1 | Thin | 125/80, 125/95, 115/85 | 53.5, 100, 63.5 | 72.3 ± 24.5 |
| Dog #1 | Thick | 210/120, 125/80, 140/110 | 46.0, 34.9, 64.9 | 48.6 ± 15.2 |
| | Double | 115/60, 115/75, 113/95 | 42.6, 47.4, 35.4 | 41.8 ± 6.0 |
| | Filled Double | 110/80, 100/75, 115/85 | 10.9, 23.5, 6.3 | 13.6 ± 8.9 |
| Leg #2 | Thin | 130/90, 164/120, 160/110 | 47.7, 44.6, 51.7 | 48.0 ± 3.5 |
| Dog #2 | Thick | 120/80, 140/100, 150/100 | 57.1, 57.0, 60.0 | 58.0 ± 1.7 |
| | Double | 140/100, 140/100, 160/140 | 36.3, 27.2, 24.7 | 29.4 ± 6.1 |
| | Filled Double | 135/80, 140/100, 160/120 | 11.7, 24.1, 1.7 | 12.5 ± 11.2 |
| Leg #3 | Thin | 95/70, 115/70, 120/70 | 54.7, 37.2, 61.3 | 51.0 ± 12.4 |
| Dog #3 | Thick | 90/70, 115/70, 95/60 | 37.7, 41.4, 41.5 | 40.2 ± 2.2 |
| | Double | 85/55, 110/70, 115/70 | 29.5, 38.0, 53.4 | 40.3 ± 12.1 |
| | Filled Double | 80/50, 80/60, 115/70 | 16.7, 13.5, 18.9 | 16.4 ± 2.7 |
| Leg #4 | Thin | 130/85, 120/75, 100/60 | 43.3, 34.4, 28.4 | 35.4 ± 7.5 |
| Dog #4 | Thick | 135/80, 115/70, 90/65 | 54.1, 32.2, 28.6 | 38.3 ± 13.8 |
| | Double | 135/80, 125/75, 120/75 | 37.1, 19.7, 30.5 | 27.1 ± 8.8 |
| | Filled Double | 125/90, 110/80, 95/65 | 22.0, 13.3, 26.3 | 20.5 ± 6.6 |

TABLE 2

EX-VIVO PERFUSION BLEEDING TESTS

| Dog # | Graft Type | Blood Pressure | Blood Weight | m = sd |
|---|---|---|---|---|
| 1 | Thin | 125/80, 125/95, 115/85 | 53.5, 100, 63.5 | 51.7 = 18.5 |
| 2 | | 130/90, 164/120, 160/110 | 47.7, 44.6, 51.7 | |
| 3 | | 95/70, 115/70, 120/70 | 54.7, 37.2, 61.3 | |
| 4 | | 130/85, 120/75, 100/60 | 43.3, 34.4, 28.4 | |
| 1 | Thick | 210/120, 125/80, 140/110 | 46.0, 34.9, 64.9 | 43.2 = 16.0 |

TABLE 2-continued

EX-VIVO PERFUSION BLEEDING TESTS

| Dog # | Graft Type | Blood Pressure | Blood Weight | m = sd |
|---|---|---|---|---|
| 2 | | 120/80, 140/100, 150/100 | 57.1, 57.0, 60.0 | |
| 3 | | 90/70, 115/70, 95/60 | 37.7, 41.4, 41.5 | |
| 4 | | 135/80, 115/70, 90/65 | 54.1, 32.5, 28.6 | |
| 1 | Double | 115/60, 115/75, 113/95 | 42.6, 47.4, 35.4 | 31.5 = 9.6 |
| 2 | | 140/100, 140/100, 160/140 | 36.3, 27.2, 24.7 | |
| 3 | | 85/55, 110/70, 115/70 | 29.5, 38.0, 53.4 | |
| 4 | | 135/80, 125/75, 120/75 | 37.1, 19.7, 30.5 | |
| 1 | Filled Double | 110/80, 100/75, 115/85 | 10.9, 23.5, 6.3 | |

TABLE 3

| GRAFT | THIN | THICK | DOUBLE | FILLED DOUBLE |
|---|---|---|---|---|
| | (grams ± s.d.)** | | | |
| | 51.7 ± 18.5* | 43.2 ± 16.0 | 31.5 ± 9.6 | 15.6 ± 7.5 |
| STATISTICS | N | t | P | |
| Filled Double vs. Double | 22 | 5.50 | <0.001 | |
| Filled Double vs. Thin | 22 | 6.11 | <0.001 | |
| Filled Double vs. Thick | 22 | 7.48 | <0.001 | |
| Thin vs. Double | 22 | 2.53 | <0.05 | |
| Thick vs. Double | 22 | 2.52 | <0.05 | |
| Thin vs. Thick | 22 | 0.74 | n.s. | |

*mean of 12 measurements in 4 legs (3 measurements/leg).
**grams of blood in 30 seconds from an 18-gauge needle puncture of the tubes.

EXAMPLE 3

Eleven dogs had a fistula constructed between the right carotid artery and the left external jugular vein, using a graft going through a subcutaneous tunnel in the posterior aspect of the neck. A 6 mm diameter conventional GORE-TEX PTFE tube 120 mm in length was used in 5 dogs and a 120 mm filled double tube prepared according to Example 1 was tested on 6 dogs. Each graft was punctured on days 1, 3-4, and 7-8 after construction of the fistula. Five minutes after removing the needle, a small incision over the puncture area was made, thereby exposing the tube. The amount of blood present was estimated by absorbing it with sponges and weighing them. The results are shown in Table 4.

In the control group, 8 punctures resulted in the loss of over 100 ml of blood. Two punctures bled between 40 and 100 ml, 2 punctures bled 20 ml and 40 ml and only one puncture bled less than 20 ml. In 10 instances, it was necessary to place a stitch in the tube in order to stop the bleeding. In the filled double tube, only 3 out of 14 punctures bled. Two bled beween 20 ml and 40 ml and the third one bled less than 20 ml. Not one puncture required stitches for hemostasis.

The results described in Examples 2 and 3 clearly demonstrate the superior characteristics of the filled double tube over conventional grafts for hemoaccess in terms of the amount of bleeding resulting from a needle puncture. This was clearly verified both in the ex vivo experiment (Example 2) and in the in vivo interposition AV fistulas (Example 3).

TABLE 4

| Dog # | Graft Type | Days of Puncture | | |
|---|---|---|---|---|
| | | 1 | 3-4 | 7-8 |
| 8006 | 6 mm Gore-Tex ® | ++++* | ++++* | clotted |
| 8060 | " | ++++* | ++* | + |
| 8064 | " | ++++ | ++++* | ++++* |
| 8065 | " | ++++* | ++++* | clotted |
| 8103 | " | ++ | +++* | +++* |
| 8005 | Double "silicone" | 0 | 0 | 0 |
| 8056 | " | ++ | 0 | 0 |
| 8061 | " | 0 | 0 | died |
| 8101 | " | 0 | + | clotted |
| 8102 | " | 0 | clotted | |
| 8099 | " | 0 | 0 | ++ |

0: no bleeding
+: 0-20 ml of blood
++: 20-40 ml of blood
+++: 40-100 ml of blood
++++: more than 100 ml of blood
*needle hole required stitch to control bleeding

I claim:

1. A filled coaxial double lumen tube for use as an implantable vascular graft in in vivo hemoaccess which comprises an outer tube positioned over an inner tube, both tubes being made of a material acceptable for use in implantable vascular grafts and having an internal and external diameter and a wall thickness, the outer tube having an internal diameter which is at least 1 mm larger than the external diameter of the inner tube creating a space between the outer tube and the inner tube and a self-sealing, nonbiodegradable, biocompatible polymer adhesive which evenly fills the space between the outer tube and the inner tube.

2. A filled double tube as described in claim 1 wherein the outer tube is shorter than the inner tube and is positioned over the center of the inner tube thereby allowing the ends of the inner tube to extend beyond each of the outer tube.

3. A filled double tube as described in claim 1 wherein the inner and outer tubes are made from a material selected from the group consisting of PTFE, synthetic polyester fiber, and reinforced PTFE and the self-sealing, nonbiodegradeable, biocompatible polymer is a silicone sealant.

4. A filled double tube as described in claim 3 wherein the outer tube is synthetic polyester fiber and the inner tube is reinforced PTFE.

5. A filled double tube as described in claim 3 wherein the outer tube has an internal diameter of about 6 mm to about 10 mm and a wall thickness of about 0.5 mm to 1 mm, and the inner tube has an internal diameter of about 4 mm to about 8 mm and a wall thickness of about 0.5 mm to about 1 mm.

6. A filled double tube as described in claim 3 wherein the outer tube has an internal diameter of about 8 mm and a wall thickness of about 1 mm and the inner tube has an internal diameter of about 6 mm and a wall thickness of about 1 mm.

* * * * *

UNITED STATES PATENT AND TRADEMARK OFFICE
CERTIFICATE OF CORRECTION

PATENT NO. : 4,619,641
DATED : October 28, 1986
INVENTOR(S) : Harry Schanzer

It is certified that error appears in the above-identified patent and that said Letters Patent is hereby corrected as shown below:

First page, Item 54, and Col. 1, first line, "ANTERIOVENOUS" should read --ARTERIOVENOUS--;

Col. 1, lines 7-8, "require" should be --requires--;

Col. 2, line 48, after "Teflon" and "Dacron", insert a --,--;

Col. 2, line 51, "are, Teflon" should read -- are Teflon,--;

Col. 2, line 52, after "Dacron" insert a --,--; and

Col. 6, line 46, after "each" insert --end--.

Signed and Sealed this

Third Day of March, 1987

Attest:

DONALD J. QUIGG

Attesting Officer

Commissioner of Patents and Trademarks